United States Patent [19]
Shetty et al.

[11] 3,974,157
[45] Aug. 10, 1976

[54] 1-(AMINO-ALKYL)-2-ARYL-CYCLOHEXANE ALCOHOLS AND ESTERS

[75] Inventors: Bola Vithal Shetty, Rockville, Md.; Telfer Lawson Thomas, Pittsford, N.Y.

[73] Assignee: Pennwalt Corporation, Philadelphia, Pa.

[22] Filed: Jan. 29, 1975

[21] Appl. No.: 545,074

Related U.S. Application Data
[63] Continuation-in-part of Ser. No. 447,804, March 4, 1974, abandoned.

[52] U.S. Cl. ............... 260/247.2 B; 260/244 R; 260/247.7 V; 260/247.7 Z; 260/268 C; 260/268 R; 260/268 PH; 260/293.83; 260/293.84; 260/307 C; 260/326.47; 260/326.5 M; 260/326.5 J; 260/327 M; 260/348 R; 260/448.8 R; 260/465 F; 260/473 A; 260/488 CD; 260/490; 260/505 E; 260/512 R; 260/520 B; 260/559 R; 260/559 D; 260/567.6 M; 260/570.5 CA; 260/592; 260/599; 260/618 R; 424/248; 424/250; 242/267; 424/274

[51] Int. Cl.² ............................. C07D 295/00

[58] Field of Search ............ 260/247.2 B, 570.5 CA, 260/293.84, 293.83, 326.47, 268 R

[56] References Cited
UNITED STATES PATENTS

| | | | |
|---|---|---|---|
| 2,586,512 | 2/1952 | Butner et al. | 260/563 |
| 2,656,386 | 10/1953 | Hogg et al. | 260/563 |
| 2,680,115 | 6/1954 | Ruddy et al. | 260/294.7 |
| 3,652,589 | 3/1972 | Flick et al. | 260/326.5 M |

*Primary Examiner*—Paul J. Killos

[57] ABSTRACT

Analgesics, local anesthetics, and antiarrhythmics which are 1-(amino-alkyl)-2-aryl-cyclohexane alcohols and esters having the structure

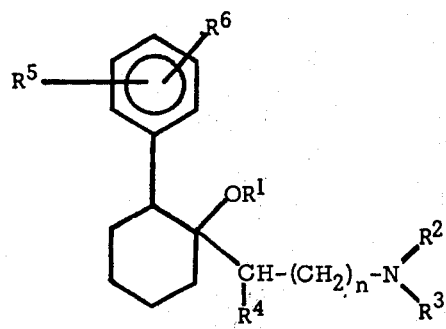

wherein
$R^1$ is hydrogen or alkanoyl; $R^2$ and $R^3$ individually are hydrogen, lower alkyl, or lower alkenyl, or $R^2$ and $R^3$ together with the nitrogen to which they are attached form a morpholine radical, a piperazine radical or a carbocyclic ring; $R^4$ is hydrogen or lower alkyl; $R^5$ and $R^6$ individually are hydrogen, lower alkyl, hydroxyl or lower alkoxy; and the pharmaceutically acceptable acid addition and quaternary salts thereof, as well as stereoisomers and optical isomers thereof. This invention relates also to processes for making and using the foregoing compounds.

24 Claims, No Drawings

1-(AMINO-ALKYL)-2-ARYL-CYCLOHEXANE ALCOHOLS AND ESTERS

This application is a continuation-in-part of our application Ser. No. 447,804 filed Mar. 4, 1974, now abandoned.

This invention relates to analgesics, local anesthetics, and antiarrhythmics which are 1-(amino-alkyl)-2-aryl-cyclohexanol compounds having the following structure:

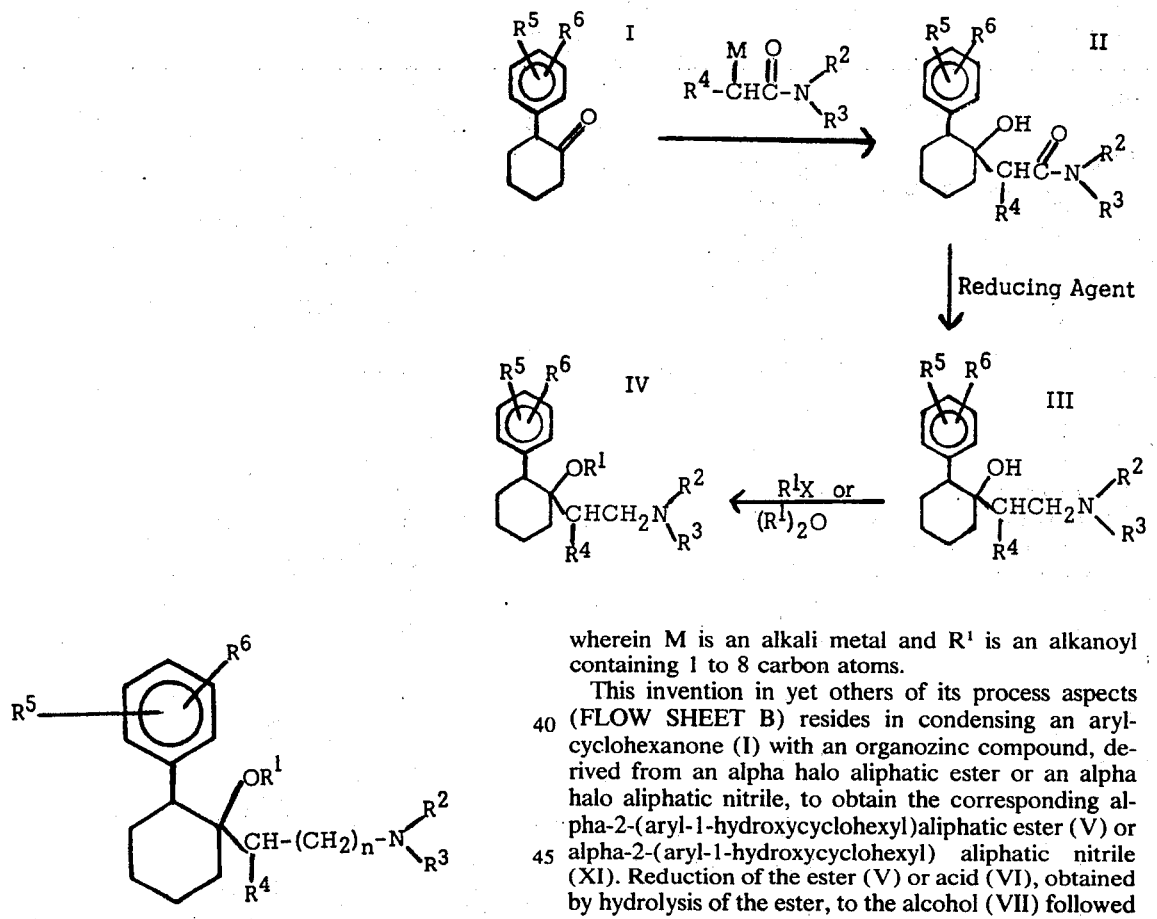

wherein
$R^1$ is hydrogen or alkanoyl (1 to 8 carbon atoms);
$R^2$ and $R^3$ individually are hydrogen, lower alkyl (1 to 8 carbon atoms), or lower alkenyl (3 to 8 carbon atoms) or
$R^2$ and $R^3$ together with the nitrogen to which they are attached form a morpholine radical, a piperazine radical or a ring structure containing 3 to 6 methylene groups;
$R^4$ is hydrogen or lower alkyl (1 to 8 carbon atoms);
$R^5$ and $R^6$ individually are hydrogen, lower alkyl (1 to 8 carbon atoms), hydroxyl or lower alkoxy (1 to 8 carbon atoms);
n is 0 or 1, and the pharmaceutically acceptable acid addition and quaternary salts thereof, as well as stereoisomers and optical isomers thereof. This invention relates also to processes for making and using the foregoing compounds.

This invention in one of its process aspects (FLOW SHEET A) resides in condensing a 2-aryl cyclohexanone (I) with an alkali metal derivative of a lower alkanoyl-(N,N-disubstituted amide), wherein the alkali metal is alpha to the carbonyl group to obtain an alpha [2-aryl(1-hydroxycyclohexyl)] lower alkanoyl-N,N-disubstituted amide (II). Reduction of the alkanoyl carbonyl group results in the 2-aryl-1-(N,N-disubstituted amino alkyl)-cyclohexanol (III) which may be alkylated with an alkanoyl halide or an alkanoyl anhydride to form the corresponding ester (IV).

FLOW SHEET A wherein M is an alkali metal and $R^1$ is an alkanoyl containing 1 to 8 carbon atoms.

This invention in yet others of its process aspects (FLOW SHEET B) resides in condensing an aryl-cyclohexanone (I) with an organozinc compound, derived from an alpha halo aliphatic ester or an alpha halo aliphatic nitrile, to obtain the corresponding alpha-2-(aryl-1-hydroxycyclohexyl)aliphatic ester (V) or alpha-2-(aryl-1-hydroxycyclohexyl) aliphatic nitrile (XI). Reduction of the ester (V) or acid (VI), obtained by hydrolysis of the ester, to the alcohol (VII) followed by esterification with an sulfonyl halide yields the sulfonic acid ester (VIII) which on reaction with ammonia or an amine, yields the desired 1-(amino or N-substituted aminoalkyl)-2-aryl-cyclohexanol (IX). The nitrile (XI) on reduction yields a 1-(aminoalkyl)-2-aryl-cyclohexanol (XII) in which the nitrogen atom is unsubstituted and which may be used as such or the nitrogen atom may be alkylated to obtain the N-substituted compounds (IX or X).

In yet another of its process aspects (FLOW SHEET C), this invention resides in reacting the acid (VI) with a halo ester and then with an alkali metal azide to produce the 6-aryl-1-oxa-3-azaspiro[4.5]decan-2-one (XIII) which can be alkylated to give the corresponding N-alkyl oxaazaspiro decan-2-one (XIV). The latter may in turn be reduced to the 1-(1-dialkylaminoalkyl)-2-aryl-cyclohexanol (XV). The correponding ester (XVI) can be formed by acylating the resulting cyclohexanol (XV) with an alkanoyl halide or with an alkanoic anhydride. Alternatively, the oxa-azaspirodecan-2-one (XIII) can be converted to the 1(1-aminoalkyl)-

2-arylcyclohexanol (XVII) by hydrolysis. In yet another alternative, the aryl-oxaazaspiro-decan-2-one (XIII) can be directly reduced to the corresponding alkyl amino alkyl cycohexanol (XVIII).

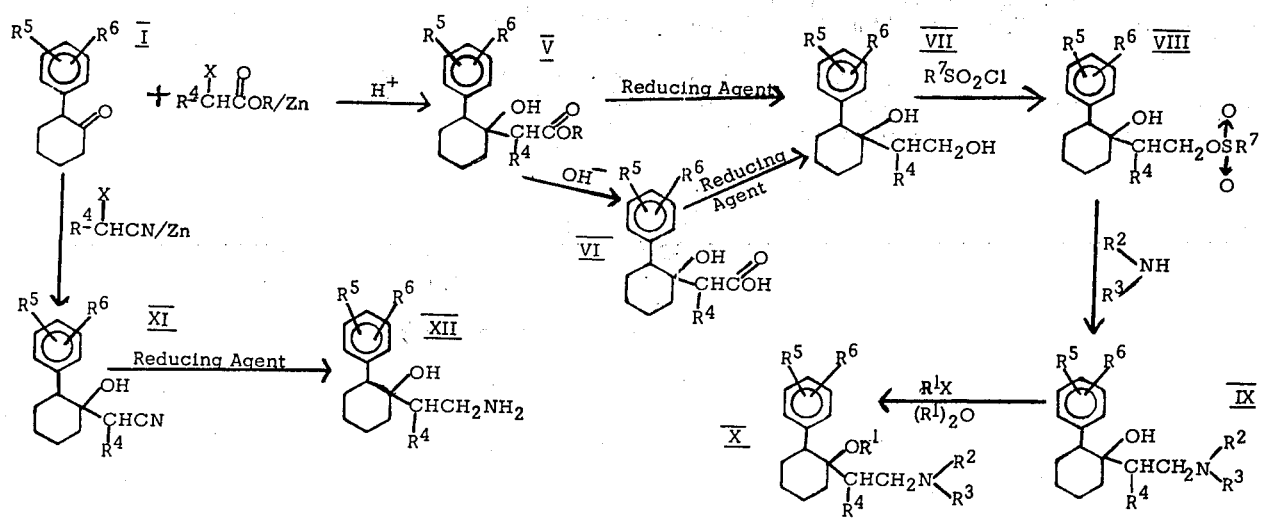

X = halogen (e.g. Cl, Br, I)
R = hydrocarbon
$R^1$ = alkanoyl (1 to 8 carbon atoms)
$R^7$ = aryl, alkyl (1-8 carbon atoms) or $F_3C$

FLOW SHEET B

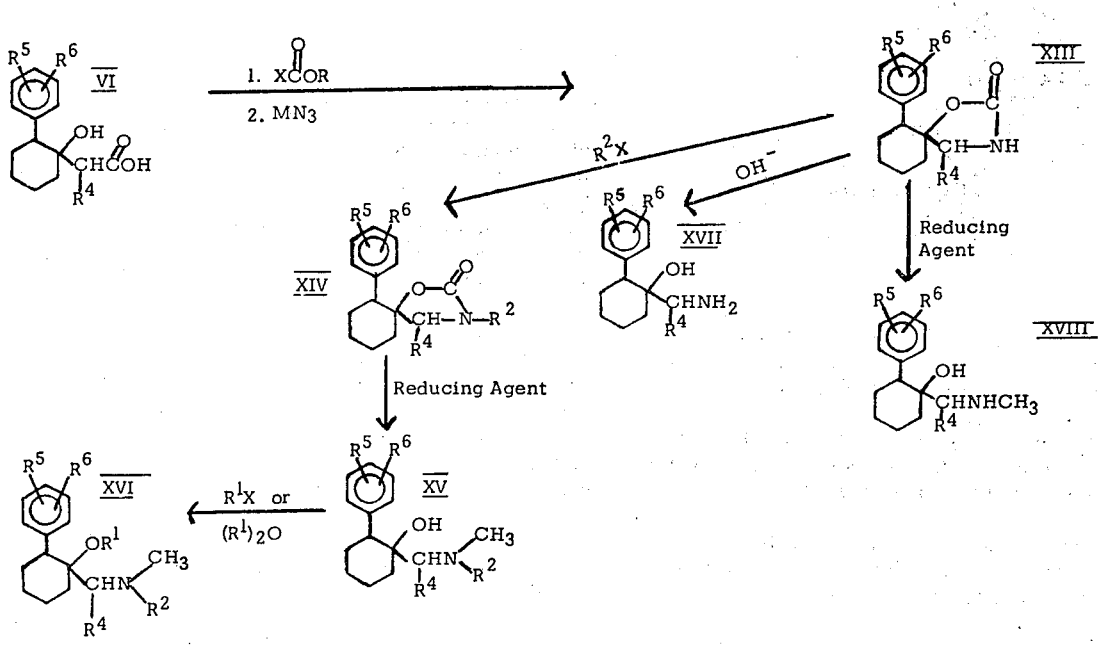

R = hydrocarbon;
$R^1$ and $R^2$ = alkanoyl (1-8 carbon atoms)
M = alkali metal

FLOW SHEET C

Other process aspects of this invention are illustrated by Flow Sheets D, E, F, G and H.

Flow Sheet D

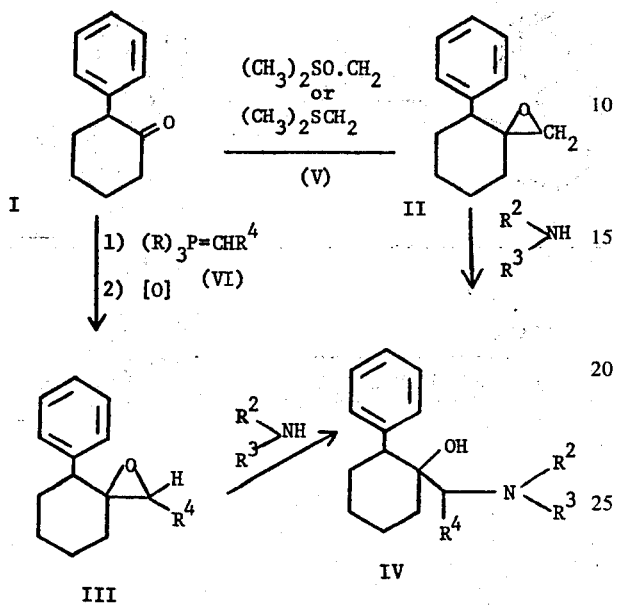

An aryl cyclohexanone (I) is condensed either with dimethyloxosulfonium methylide or dimethylsulfonium methylide (V), or with the methylene or ethylene Wittig reagent (VI) followed by oxidation, to give the epoxides II and III which are reacted with appropriate amines to give the corresponding 1-aminoalkyl-2-arylcyclohexanols (IV).

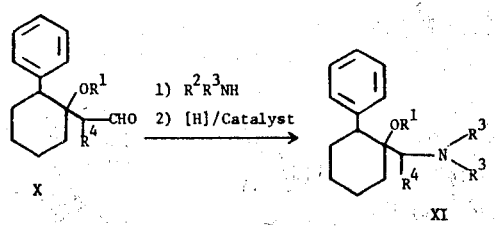

The epoxide III is condensed with the lithium salt of a 1,3-dithiane or the ketone I is reacted with a dihydro-1,3-oxazine to give (VII) and (VIII) respectively which are readily converted to the aldehydes by procedurs known to the art. The resulting hydroxy-aldehydes (IX) can be converted directly to the amines (XI) by reductive-amination procedures or may be first esterified and then converted to the amines (XI).

Flow Sheet E

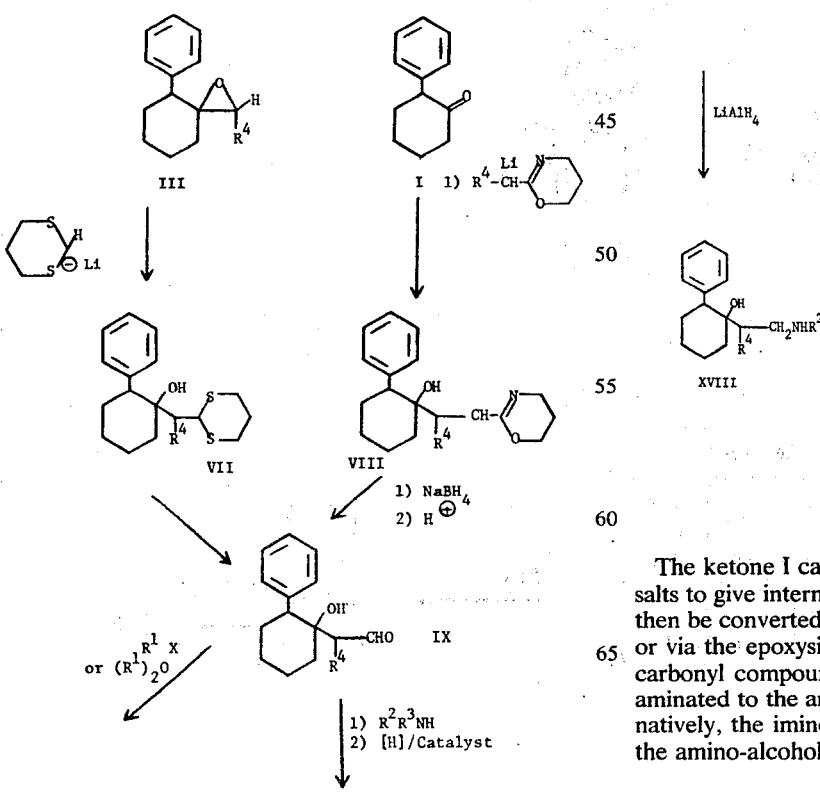

Flow Sheet F

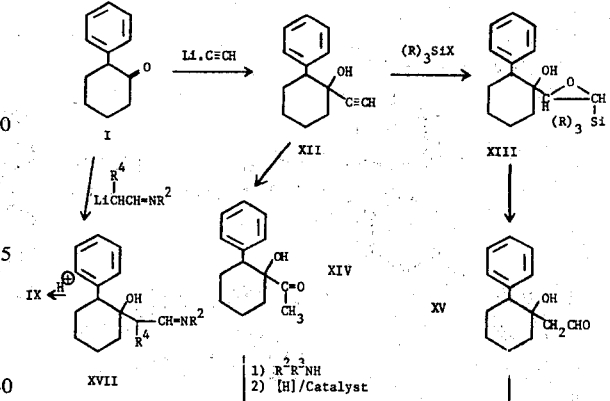

The ketone I can be condensed with various lithium salts to give intermediates (XII) and (XVII) which can then be converted to ketones (XIV) or aldehydes (IX) or via the epoxysilanes (XIII) to aldehyde (XV). The carbonyl compounds can subsequently be reductively aminated to the aminoalcohols (XI) and (XVI). Alternatively, the imine (XVII) can be reduced directly to the amino-alcohol (XVIII).

Flow Sheet G

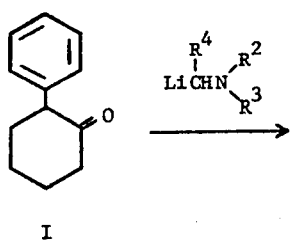

A further process is the direct alkylation of the 2-arylcyclohexanone (I) with the lithium salt of an amine to give the amino-alcohols (IV).

(XXI) can also be obtained by addition of the lithium salt of the diphenylmethane imines (XXIII) to ketone (I) followed by hydrolysis.

Flow Sheet J

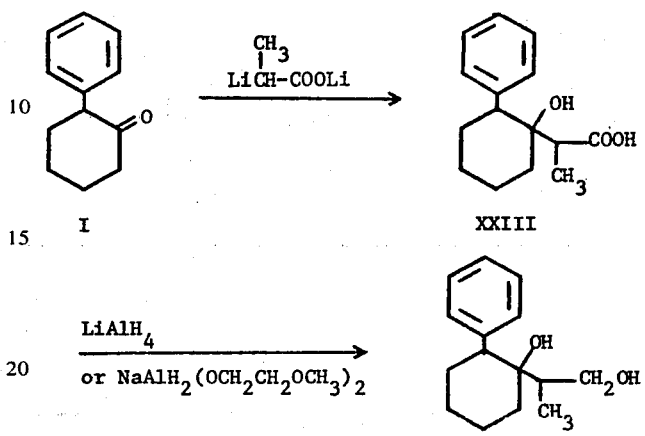

Flow Sheet H

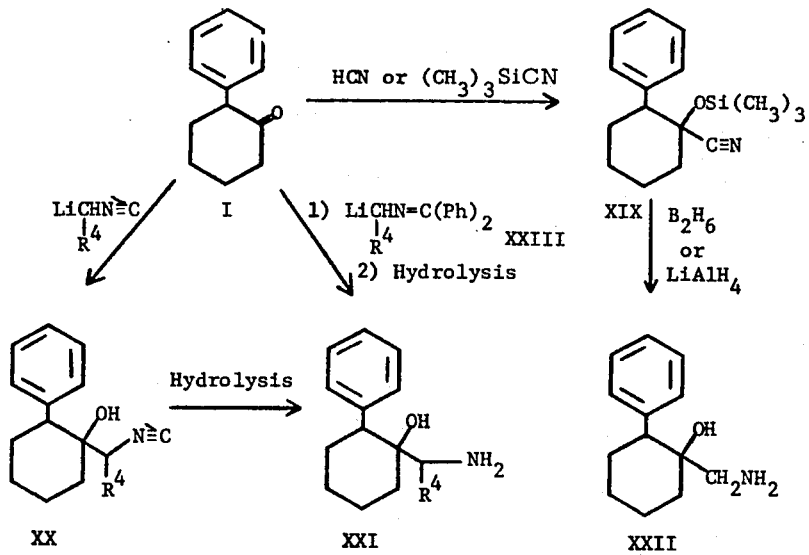

The invention is further illustrated by these processes for preparing examples where the amino group is primary. The addition of cyanide to I using hydrogen cyanide or trimethyl silyl cyanide affords the cyanohydrin (XIX) which can be reduced to the amino alcohol (XXII) by borane or lithium aluminum hydride.

The lithium salt of an alkyl isocyanide adds to I to give the isocyanide-alcohol (XX) which can be hydrolyzed to the amino-alcohol (XXI). The amino-alcohol

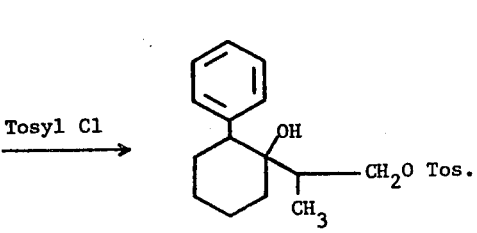

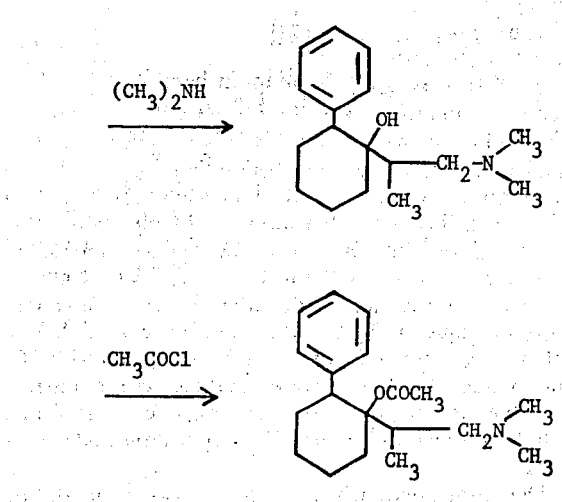

EXAMPLE A

2-(1-Hydroxy-2-phenylcyclohexyl)-propionic acid

A solution of 177 ml (0.89 moles, m.w.=181.31, 161 gm) dicyclohexylamine in 1080 ml THF was cooled in a MeOH/dry ice bath to <0° and a solution of 370 ml n-butyl lithium (2.2 molar solution in hexane, 0.89 moles) was added at ≤0°. After about 5 minutes, a solution of 33.2 ml (0.445 mole, m.w.=74.08) propionic acid in 280 ml THF was added at ≤0°, then the solution was heated to about 50° over 1½ hours. After cooling the mixture back to −50°, a solution of 75.5 gm (78% pure, = 56.6 gm pure ketone, 0.325 mole, m.w.=174.24) in 200 ml THF was added as rapidly as possible. Temperature rose to about −25°. The reaction mixture was allowed to warm to room temperature, at which point the reaction was complete.

The reaction mixture was added to 1100 ml water, then 1400 ml ethyl acetate was added and the mixture extracted with a solution of 560 gm citric acid in 700 ml water, then twice with 500 ml dilute citric acid solution (ca 10%) and once with 500 ml water.

The aqueous extracts were extracted with 2 × 200 ml ethyl acetate, and this was washed twice with 400 ml water. The organic extracts were combined and extracted with 300 ml 10% K$_2$CO$_3$ solution. The aqueous solution was washed with 2 × 300 ml ethyl acaetae. The aqueous solution was acidified and extracted with 4 × 300 ml ethyl acetate and dried over MgSO$_4$. Removal of solvent left 95 gm crude product. Yield ~ quantitative.

The crude product was dissolved in 190 ml CCl$_4$ and to the solution was added 320 ml hexane. The mixture was allowed to crystallize, the crystalline material was filtered off and washed with hexane. Wgt=29.9 gm "major isomer".

Removal of solvent from the filtrate gave 60.5 gm of a resinous mixture of "major" and "minor" isomers.

2(1-Hydroxy-2-phenylcyclohexyl)-propanol "minor" isomer

The mixture of "major" and "minor" acid isomers from the preceding preparation (60.5 g, 0.244 mole, m.w.=248.33) was dissolved in 240 ml THF and added dropwise to a solution of 16.5 gm (0.43 mole, m.w.=38) LAH in 265 ml THF. The reaction mixture was refluxed for 2 hours, then cooled to ca.0° and the excess LAH decomposed with 120 ml ethyl acetate, after which a solution of 87 ml H$_2$O in 87 ml THF was carefully added. After stirring a few minutes, the mixture was filtered and the cake washed thoroughly with THF. The solution was dried over MgSO$_4$ and the solvent removed on the rotovap. Crude wt = 46.7 gm.

The mixture was dissolved 140 ml of a 1:1::cyclohexane:hexane mixture and seeded with a few crystals of pure "minor" diol. Crystallization of the "minor" diol commenced rapidly. After a few hours, the crystals were filtered off and washed with solvent. Wgt = 8.6 gm, m.p. = 94°–96°.

The filtrate was about a 1:1 mixture of "major" and "minor" diols. Attempted crystallization of more "minor" diol by cooling the filtrates resulted in crystallization of a mixture (ca 1:1) of the two diols. The diols could be completely separated by chromatographing on SiO$_2$ (100 gm dry column SiO$_2$/gm mixture, developing with 20% EtAc in cyclohexane).

2-(1-Hydroxy-2-phenylcyclohexyl)-propyl p-toluenesulfonate, "minor" isomer

This was prepared from the "minor" diol and p-toluenesulfonyl chloride in pyridine using exactly the same procedure as for the preparation of the "major" tosylate. (Example II)

1-(2-Dimethylamino-1-methylethyl)-2-phenylcyclohexanol "minor" isomer

Dimethylamine (14 ml, 9.3 gm, 0.2 mole, m.w.=45.09, neat liquid) was added to a solution of 13.3 g (0.034 mole, m.w.=388.51) of the "minor" tosylate in 80 ml DMSO in a pressure bottle. The mixture was heated under head pressure at 80° for 5 hours.

The reaction mixture was cooled to room temperature, added to 900 ml water and extracted 5 times with 200 ml CCl$_4$. The CCl$_4$ layer was washed with water and then extracted with 100 ml 7% HCl and twice with 75 ml 3.5% HCl. The aqueous layer was washed with CCl$_4$, then basified with NaOH and the product extracted into CCl$_4$. The CCl$_4$ was dried over MgSO$_4$ and the solvent removed on the rotovap leaving 6.1 gm product.

1-(2-Dimethylamino-1-methylethyl)-2-phenylcyclohexyl acetate, "minor" isomer Acetyl chloride (2.7 ml, 3 gm, 0.038 mole, m.w.=78.50) was added to a solution of 6.1 gm (0.023 mole, m.w.=261.42) "minor" aminoalcohol in 70 ml CHCl$_3$. Stirred 45 min, then added 60 ml 10% NaOH and stirred vigorously for a few minutes. Allowed to stand for 1 min, then added, with slow stirring, under the CHCl$_3$ layer, 3 ml AcCl. Allowed to stand 30 min, then stirred vigorously again for a few minutes, allowed to stand 1 min and added 3 ml more AcCl with gentle stirring. After 1 hour, most of the alcohol had reacted. Separated the CHCl$_3$ layer and extracted the aqueous layer with 3 × 25 ml CHCl$_3$. Dried, filtered and added 7 ml AcCl. Relatively little change on standing overnight. Added 15 ml MeOH, allowed to stand for about an hour, extracted with dil NaOH, dried and removed the solvent on the rotovap. Crude wt = 5.9 gm tlc (20% EtAc in cyclohexane on ammonia treated SiO$_2$) showed product, RF=0.27, small amount of "major" isomer, Rf=0.36, and traces of three impurites, Rf$^2$ 0.55, 0.68 and 0.96.

Dissolved in 18 ml i-PrOH filtered, rinse-washed with 6 ml i-PrOH, acidified with gaseous HCl and diluted with 1000 ml Et$_2$O. Allowed to crystallize, filtered and washed with i-PrOH/ET$_2$O. Wgt = 3.5 g, m.p. =173°–175°C.

The compounds of this invention may exhibit geometrical or optical isomerism and may be obtained as mixtures of the isomers. The isomers may be separated from their mixture by well-known techniques, e.g. by chemical, mechanical or biological methods.

The invention in another of its process aspects resides in using the compounds of this invention as analgesic, local anesthetic or anti-arrhythmic agents.

The compounds of this invention in the form of their free base or acid addition and quaternary salts thereof, possess the characteristic of exerting ananalgesic, local anesthetic or antiarrhythmic effects and therefore as such are therapeutically useful.

The alkanoyl substituents include, for example, acetyl, propionyl, butyryl and their branched chain analogues, e.g., pivalyl and alpha methylpropionyl.

The lower alkyl substituents ($R^2$, $R^3$, $R^4$) include such monovalent radicals as ethyl, propyl, butyl and such other straight and branched chain aliphatic hydrocarbon radicals having 1 to 8 carbon atoms, but preferably methyl.

When $R^2$ and $R^3$, together with the nitrogen atom to which they are attached, form a cyclic amino structure, the resulting heterocyclic radical includes piperidino, pyrrolidino, morpholino, and phenylpiperazinyl, etc. The lower alkenyl radicals include allyl, butenyl, etc.

The alkoxy substituents include, for example, methoxy, ethoxy, propoxy, butoxy, and the like.

The acid addition salts include those prepaed from such acids as hydrochloric acid, phosphoric acid, sulfuric acid, maleic acid, citric acid, p-toluenesulfonic acid and other well-known pharmaceutically acceptable acids. The quaternary salts include those prepared from such organic halides as methyl iodide, ethyl idoide, benzyl chloride and the like.

In general, the amino-cyclohexanols of this invention are prepared by the synthetic schemes set forth in the examples which are illustrative of the processes employed to prepare the composition aspect of this invention. In the examples, percent concentrations (e.g. 10% $H_2SO_4$) are percent by weight; percent yields are mol percents, and temperatures (e.g. reaction temperatures melting points, etc.) are in degrees Centigrade.

EXAMPLE I

Preparation of 1-(2-Dimethylamino-1-methylethyl)-2-phenylcyclohexanol.

Synthetic Scheme:

To one mole of phenyl lithium in benzene-ether solution (ca 2M), diluted with 1000 ml ether, add a solution of 100 ml dimethylamine in 200 ml ether over about 15 minute period, then reflux for 15 minuts. Then add a solution of 100 ml N,N-dimethylpropionamide in 200 ml ether over about 15 minutes. Following an additional 15 minute reflux period, add a solution of 175 g of 2-phenylcyclohexanone in 200 ml ether during about ½ hour period. Reflux the reaction mixture 2 hours, cool to 0° and treat all at once with 1000 ml 3N-hydrochloric acid. The ether layer is separated from the aqueous layer and the latter is extracted with ether. The combined ether layers are washed with 3N-hydrochloric acid, then water, and last with potassium bicarbonate solution. After drying over magnesium sulfate, remove the solvent by evaporation under vacuum.

The crude amide which results is dissolved in 200 ml ether and added to 40 grams lithium aluminum hydride in 500 ml ether over about ½ hour period. After a 2½ hour reflux, the mixture is cooled to −5° and the excess lithium aluminum hydride is destroyed with 300 ml ethyl acetate. Add 200 ml water, filter the resulting slurry and wash the filter cake with ether. Extract the ether with dilute hydrochloric acid. The acid layer is then made basic to litmus using sodium hydroxide solution and is extracted with chloroform. After evaporation of the chloroform, 42.5 grams of crude product is obtained as a residue.

This product is a mixture of two geometrical isomers which is separated into two isomers by chromatography on $SiO_2$ giving 31.0 grams major isomers and 5.2 grams minor isomer, both distilling at 97°–105° at 0.005 mm.

EXAMPLE I (a)

1-(2-Dimethylamino-1-methylethyl)-2-phenylcyclohexyl propionate maleate (Major Isomer)

The propionate ester of the major isomer is prepared by dissolving 16 grams of 1-(2-dimethylamino-1-methylethyl)-2-phenyl-cyclohexanol (major isomer) in 100 ml of chloroform and adding 16 grams of propionyl chloride. After standing for 2 hours, the soluion is concentrated by evaporation under vacuum to a thick paste which is shaken with 200 ml ether. The propionate ester is obtained as the hydrochloride salt. Conversion of hydrochloride salt to the maleate salt yields 10 grams of product meltig at 163°–165°C.

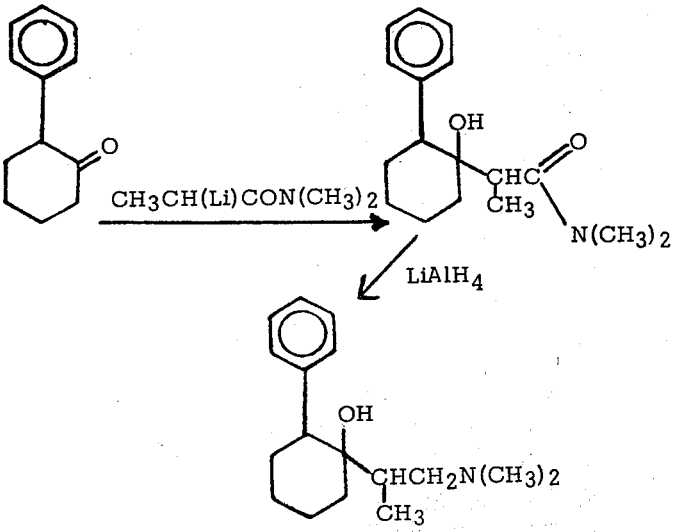

EXAMPLE I (b)

1-(2-Dimethylamino-1-methylethyl)-2-phenylcyclohexyl propionate maleate (Minor Isomer)

The procedure of Example I(a) is followed using 10 grams of 1-(2-Dimethylamino-1-methylethyl)-2-phenylcyclohexanol (minor isomer) and 6 grams propionyl chloride. The resulting propionate ester, obtained as the hydrochloride salt, is contaminated with alcohol and is purified by chromatography on silica gel. Conversion to the maleate salt yields 3.5 grams product, melting at 104°–105°C.

EXAMPLE I (c)

1-(2-Dimethylamino-1-methylethyl)-2-phenylcyclohexyl acetate maleate (Major Isomer)

The procedure of Example I (a) is followed using 12 grams of 1-(2-Dimethylamino-1-methylethyl)-2-phenylcyclohexanol (major isomer) and 4.2 grams of acetyl chloride. Conversion of the resulting acetate hydrochloride salt to the maleate salt yields 11 grams of product. After recrystallization from isopropanol, the melting point is 170.5° to 172°C.

EXAMPLE II

Preparation of
1-(1-Methyl-2-piperidinoethyl)-2-phenylcyclohexanol.

Synthetic Scheme:

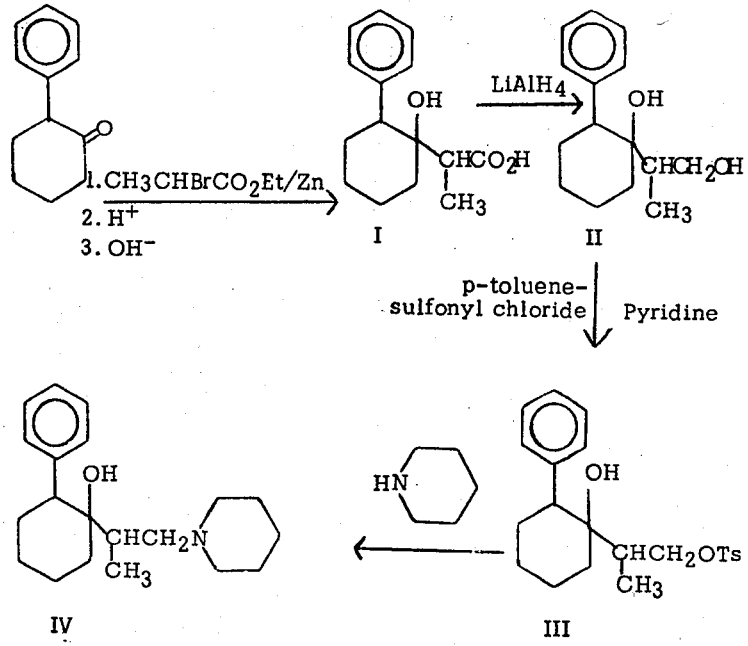

Preparation of
2-(1-Hydroxy-2-phenylcyclohexyl)-propionic acid (I)

2-Phenylcyclohexanone (100 grams) and 111 grams of ethyl 2-bromopropionae are dissolved in 225 ml benzene plus 225 ml toluene. Freshly activated zinc dust (38.4 grams) is added and the mixture heated to reflux with stirring. The vigorous reaction, which commences soon after refluxing begins, is moderated with an ice bath. After the initial reaction is over (about 5 minutes), the mixture is refluxed for 1½ hours, then cooled and added to 1000 ml ice cold 10% sulfuric acid. The aqueous layer is extracted with benzene and the combined organic layer is washed with water and potassium bicarbonate solution. The solvent is removed by evaporation under vacuum and the crude ester hydrolyzed by refluxing for three hours in a mixture of 360 ml methanol, 1080 ml water, and 225 ml of 50% sodium hydroxide solution. The hydrolysate is cooled and extracted with chloroform, to remove unreacted 2-phenylcyclohexanone.

The aqueous solution is acidified and the product extracted therefrom with chloroform. The chloroform layer is washed with water, dried with magnesium sulfate and the solvent is removed by evaporation leaving 116.5 grams of acid (I). Recrystallization of I from 800 ml cyclohexane yields 110 grams product melting at 1298°–130°C.

Preparation of
2-(1-Hydroxy-2-phenylcyclohexyl)-propanol (II)

A solution of 61 grams of 2-(1-hydroxy-2-phenylcyclohexyl)-propionic acid (I) in 200 ml tetrahydrofuran is added dropwise to 30 grams of lithium aluminum hydride in 700 ml ether. After refluxing for 2½ hours, the mixture is cooled to −5° and treated successively with 140 ml ethyl acetate and 150 ml water. The slurry is filterd, the residue on the filter paper is washed well with ether which is combined wiht the filtrate and the solutin dried over magnesium sulfate. Evaporation of the solution left 57 grams of product (II) melting at 89°–93°C.

Preparation of
2-(1-Hydroxy-2-phenylcyclohexyl)-propyl-p-toluenesulfonate (III)

A solution of 57 grams of 2-(1-hydroxy-2-phenylcyclohexyl)-propanol (II) in 350 ml pyridine is treated with 72 grams of p-toluenesulfonyl chloride and the mixture is stirred at room temperature for 40 hours. It is then poured into 1500 ml cold water and the product extracted into chloroform. The chloroform solution is washed with dilute hydrochloric acid plus ice water, and finally with potassium bicarbonate solution. After drying over magnesium sulfate and removal of the solvent by evaporation under vacuum, 79 grams of product (III) melting at 100°–105°C is obtained.

Preparation of
1-(1-Methyl-2-piperidinoethyl)-2-phenylcyclohexanol (IV)

A solution of 18 grams 2-(1-hydroxy-2-phenylcyclohexyl)-propyl-p-toluenesulfonate (III) and 15 ml piperidine in 150 ml dimethylsulfoxide is heatd at 75° for 5 hours. The solution is then added to 1000 ml water and extracted with n-hexane. The hexane solution is washed with water, dried over magnesium sulfate and the solvent removed by evaporation under vacuum leaving 14.1 grams of product. The hydrochloride salt is made by passing dry hydrogen chloride into an ether or hexane solution of the free base. The salt is filterd and washed with ether giving the product (IV) melting at 239°–240°C.

EXAMPLE III

Preparation of
1-(1-Methyl-2-pyrrolidinoethyl)-2-phenylcyclohexanol.

The procedure of example II is repeated in all essential details with the exception that 15 ml pyrrolidine is substituted for the 15 ml piperidine. The yield of product is 14.1 grams which melts at 253°–253.5°C (hydrochloride salt).

EXAMPLE IV

Preparation of
2-(1-Hydroxy-2-phenylcyclohexyl)-2-methylethylamine.

Synthetic Scheme:

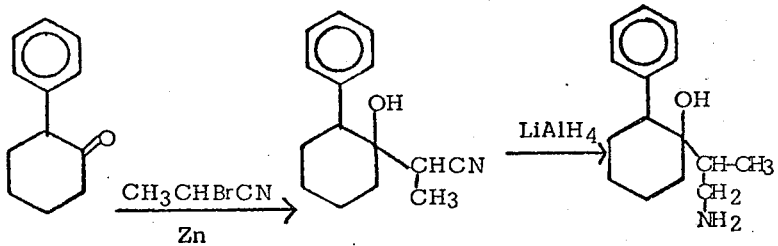

2-Phenylcycohexanone (15.9 grams) and 9.9 ml 2-bromopropionitrile is dissolved in 25 ml tetrahydrofuran and 7.3 grams of freshly activated zinc dust is added. The mixture is cooled to 8°C and 0.3 grams of HgCl₂ is added. The temperature rises to 32°C with ice bath cooling. When the temperature starts to fall, the ice bath is removed and heating commenced. The reaction may become mildy exothermic again at about 70°C. After the initial reaction is over, the mixture is refluxed for 15 minutes, cooled and added to 300 ml of 5% hydrochloric acid and ice. This mixture is extracted with chloroform and after washing the resulting solution and evaporating the solvent, 20 grams of semisolid brown material is obtained.

The above material is dissolved in 400 ml ether and 100 ml n-hexane, filtered, and added dropwise to 6 grams of lithium aluminum hydride in 250 ml ether. After refluxing for 3 hours, the mixture is cooled to −5°C and treated successively with 30 ml ethyl acetate and 30 ml water. The mixture is filtered and the solid washed with ether. The ether solution is extracted with dilute hydrochloric acid. The acid solution is made basic and the product was extracted into chloroform. The solution is washed with water, dried over magnesium sulfate and the solvent evaporated under vacuum leaving about 8.7 grams of crude product which contains two geometrical isomers plus small amounts of impurities. The isomers are separated by chromatographing on silica gel, giving 3.5 grams of the major isomer and 1 gram of the minor isomer. A cyclohexylsulfamate salt of the major isomer is made and found to melt at 98°–100°C.

EXAMPLE V

Preparation of
[2-(1-Hydroxy-2-phenylcyclohexyl)-propyl]-trimethylammonium iodide.

A solution of 3.5 grams of 1-(2-dimethylamino-1-methylethyl)-2-phenyl-cyclohexanol in 250 ml ether and 10 ml tetrahydrofuran is treated with 6 ml methyl iodide and allowed to stand for 7 days. The crystalline product is filtered and washed with ether and recrystalized from water giving 2.1 grams melting at 155°–159°C.

EXAMPLE VI

Resolution of
d,l-2-(1-Hydroxy-2-phenylcyclohexyl)-propionic acid.

The optically active alcohols and esters of this invention can be prepared from the optically active intermediate 2-(1-hydroxy-2-aryl cyclohexyl)-propionic acids, in turn prepared by the resolution of the corresponding d,l-acid.

A solution of dehydroabietylamine (263 gm) in 810 ml methanol is added to a solution of 230 gm d,l-2-(1-hydroxy-2-phenylcyclohexyl)-propionic acid in 800 ml methanol and the resulting solution is brought to persistent cloudiness with 365 ml water, then made clear again with 185 ml methanol. The solution is stored at 8° for 24–48 hours, then filtered and the solid washed with acetone, collecting the wash separately from the mother liquor.

The acetone insoluble fraction is recrystallized three times from methanol-water mixture (40 ml boiling methanol/gm to dissolve salt, followed by 6 ml water/gm salt added to the cooled methanol solution). After each recrystallization, the crystalline salt is filtered off and washed with 5:1::methanol:water mixture. The yield of resolved salt is 82 gm.

$$[\alpha]^{25°}_{365} = +5.4° (c\ l, CH_3OH).$$

Further recrystallizations of this salt gives no further change in optical rotation.

The salt is decomposed with dilute sodium hydroxide and the free amine is extracted into chloroform. The resolved acid is precipitated with dilute hydrochloric acid, extracted into chloroform, washed with water, dried over magnesium sulfate and the solvent is removed in vacuo leaving 37 gm of acid with $$[\alpha]^{25°}_{365} = -196°(c\ l\ CHCl_3).$$

The mother liquor from the original crystallization and the first recrystallization are combined and the methanol is removed on a rotary evaporator. The salt is filered off and washed with acetone, giving 165 gm of salt with $$[\alpha]^{25°}_{365} = +79° (c\ l, CH_3OH).$$

This salt is dissolved in 8500 ml methanol, cooled, diluted with 3900 ml water, stirred for several hours and filtered.

Removal of methanol from the mother liquor, followed by filtering and drying the salt gives 81 gm of partially resolved material with $$[\alpha]^{25°}_{365} = +89.1° (c\ l, CH_3OH).$$

The partially resolved (+)− acid is obtained as described on the preceding page for the (−)− acid, yielding 32 gm product with $$[\alpha]^{25°}_{365} = +103° (c\ l, CHCl_3).$$

EXAMPLE VII

Preparation of
(−)−1-(2-Dimethylamino-1-methylethyl)-2-phenylcyclohexanol.

The preparation is identical to the last four steps (I → II → III → IV) in Example II, except that (−)-2-(1-hydroxy-2-phenylcyclohexyl)-propionic acid is used in place of the d,l-acid (I in Example II) and dimethylamine is used in place of piperidine in going from III → IV of Example II. The free amino alcohol has the following optical rotation:

$$[\alpha]^{25°}_{589} = -5.1°; (c\ l;\ CHCl_3).$$

EXAMPLE VIII

Preparation of
(+)-1-(2-Dimethylamino-1-methylethyl)-2-phenylcyclohexanol

The procedure is identical to that used in Example VII except that (+)-2-(1-Hydroxy-2-phenylcyclohexyl)-propionic acid is used in place of (−)-2-(1-Hydroxy-2-phenylcyclohexyl)-propionic acid. The free amino alcohol has the following optical rotation:

$$[\alpha]^{25°}_{589} = +4.3°; (c\ l, CHCl_3).$$

EXAMPLE IX

Preparation of
(−)-1-(2-Dimethylamino-1-methylethyl)-2-phenylcyclohexyl acetate.

(−)-1-(2-Dimethylamino-1-methylethyl)-2-phenycyclohexanol (8 gm) in 65 ml chloroform is cooled to 0° and 2.7 ml acetyl chloride is added at ≤ 5°. After warming to room temperature, the solution is extracted with dilute aqueous sodium hydroxide, washed with water and dried over magnesium sulfate. The dried chloroform solution is then cooled to 0° and treated with another 3.0 ml acetyl chloride at ≤ 5° and again allowed to warm to room temperature, extracted with dilute sodium hydroxide, washed with water and dried over magnesium sulfate. Removal of solvent leaves 9.3 gm of an oil which crystallizes spontaneously. This is recrystallized from 30 ml n-hexane (at −50°) yielding 5.7 gm product melting at 63°–66°. The optical rotation is as follows:

$$[\alpha]^{25°}_{589} = -76.7°; (c\ l, CHCl_3).$$

EXAMPLE X

Preparation of
(+)-1-(2-Dimethylamino-1-methylethyl)-2-phenylcyclohexyl acetate.

The procedure used is identical to that used in Example IX except (+)-1-(2-Dimethylamino-1-methylethyl)-2-phenylcyclohexanol is used in place of (−)-1-(2-Dimethylamino-1-methylethyl)-2-phenylcyclohexanol, and the product is isolated as the hydrochloride salt by precipitation with gaseous hydrogen chloride of an ether solution of the free amine: m.p. = 150°–153°. The optical rotation is given below:

$$[\alpha]^{25°}_{589} = +29.1°; (c\ l, CHCl_3).$$

EXAMPLE XI

Preparation of
1-(2-Dimethylamino-1-methylethyl)-2-phenylcyclohexanol-p-toluenesulfonate.

A solution of 3.6 g 1-(2-Dimethylamino-1-methylethyl)-2-phenylcyclohexanol (Example I) in 30 ml acetone is added to a solution of 3.6 g p-toluenesulfonic acid. The solution is seeded and diluted after a few minutes with 75 ml dry ether to give 5 g crude product which is recrystallized from 50 ml acetone to give 4.2 product, m. 140°–2°.

EXAMPLE XII

Preparation of
1-(1-Methyl-2-piperidinoethyl)-2-phenylcyclohexyl acetate hydrochloride.

A solution of 6.6 g 1-(1-Methyl-2-piperidinoethyl)-2-phenylcyclohexanol (Example II) in 150 ml benzene is treated with 11.5 ml methyl lithium (2 molar in ether), stirred ½ hr, added another 1.5 ml methyl lithium solution, then 5 ml acetic anhydride is added and the mixture stirred for 48 hours. The mixture is added to 400 ml water and 50 ml concentrated $NH_4OH$ and extracted with benzene, the benzene extract washed with water, dried and concentrated. The residue is chromatographed on alumina (dry column) to give 3 g product which is converted to the hydrochloride salt to give 2.9 g., m. 155°–9°.

EXAMPLE XIII

Preparation of
1-(2-Allylmethylamino-1-methylethyl)-2-phenylcyclohexyl acetate.

a.
1-(2-Allylmethylamino-1-methylethyl)-2-phenylcyclohexanol.

The procedure of Example II is followed except that piperidine is replaced by allylmethylamine. Starting with 12 g allylmethylamine and 30 g of tosylate (Compound III), 5.9 g of product is obtained.

EXAMPLE XXII

Preparation of
1-(1-Methyl-2-pyrrolidinoethyl)-2-phenylcyclohexyl acetate sulfate.

1-(1-Methyl-2-pyrrolidinoethyl)-2-phenylcyclohexanol hydrochloride (Example III) is converted to the free base with NaOH and extracted into chloroform. The chloroform solution is trated with 10 ml acetyl chloride according to the procedure in Example I(c) using a reaction time of 6 hours. The HCl salt is converted to the free base and 7 g of base is treated with 7 ml sulfuric acid in ether to give the sulfate salt which is recrystallized from 20 ml isopropanol and 50 ml tetrahydrofuran to give 3.1 g crude product. The sulfate salt (7.5 g) is recrystallized from 40 ml isopropanol and 200 ml tetrahydrofuran to give 7 g., m. 154°–4.5°.

EXAMPLE XXIII

Preparation of
1-(1-Aminoethyl)-2-phenylcyclohexanol hydrochloride.

a. 4-Methyl-6-phenyl-1-oxa-3-azaspiro [4.5] decan-2-one.

2-(1-Hydroxy-2-phenylcyclohexyl) propionic acid (Example II, Compound I) (33 g) in 110 ml acetone is teated with 20.5 ml triethylamine. The solution is cooled to −5° and 14 ml ethyl chloroformate in 35 ml acetone added at a temperature below 0°. The mixture is stirred 10 minutes and 17.2 g of sodium azide in 50 ml water is added at or below 0°. The mixture is stitted 1½ hours, added to 500 ml ice water and extracted with toluene. The extract is dried and heated at 100° until the evolution of nitrogen is above over, then refluxed 2 hours, concentrated to a slurry on the rotovap and the solid filtered and washed with benzene and cyclohexane to give 28.8 g of 4-methyl-6-phenyl-1-oxa-3-azaspiro [4.5] decan-2-one, m. 171°–3°.

b. 1-(1-Aminoethyl)-2-phenylcyclohexanol hydrochloride.

4-Methyl-6-phenyl-1-oxa-3-azaspiro [4.5] decan-2-one (8 g) is refluxed with 30 ml alcohol, 15 ml water, and 15 ml 50% NaOH for 20 hours, cooled, added to 150 ml water and extracted with chloroform. The extract is washed with water, dried and concentrated. The residue is dissolved in 10 ml isopropanol, acidified with HCl gas and 5 ml ether added. When crystallization starts, another 15 ml ether is added to give 4.3 g product, m. 247°–5°.

EXAMPLE XXIV

Preparation of
1-(1-Methylaminoethyl)-2-phenylcyclohexanol hydrochloride.

4-Methyl-6-phenyl-1-oxa-3-azaspiro [4.5] decan-2-one (Example XXIII) (5 g) in 60 ml tetrahydrofuran is added to 1.6 g $LiAlH_4$ in 100 ml tetrahydrofuran. The mixtutre stirred for 65 hours. The mixture is cooled, 8 ml water added and the solid is filtered off. The filtrate is dried and concentrated. The residue is dissolved in ether and the solution acidified with HCl gas to give the HCl salt which is dissolved in 10 ml isopropanol and 50 ml ethanol, cooled, diluted with 150 ml ether to give 4.4g. product, m. 235°–7°.

EXAMPLE XXV

Preparation of
1-(2-Dimethylamino-1-methylethyl)-2-(p-methoxyphenyl)-cyclohexylacetate hydrochloride.

1-(2-Dimethylamino-1-methylethyl)-2-(p-methoxyphenyl)cyclohexanol (Example XVII) (10 g) is treated with 20 ml acetyl chloride according to the procedure of Example I(c) with a reaction time of 8 hours. The crude HCl salt was recrystallized from 25 ml isopropanol and 125 ml ether to give 3.5 g product, m. 190°–2°.

EXAMPLE XXVI

Preparation of
1-(2-Methylamino-1-methylethyl)-2-phenylcyclohexanol hydrochloride.

The procedure of Example II is followed except that piperidine is replaced by methylamine. By this method, 47.5 g 2-(1-Hydroxy-2-phenylcyclohexyl)propyl-p-toluenesulfonate and 80 ml methylamine gives 28.5 g base which is converted to the hydrochloride salt to give 26.5 g product, m. 225–6.

EXAMPLE XXVII

Preparation of
1-(1-Dimethylaminoethyl)-2-phenylcyclohexanol hydrochloride.

a. 3,4-Dimethyl-6-phenyl-1-oxa-3-azaspiro [4.5] decan-2-one

4-Methyl-6-phenyl-1-oxa-3-azaspiro [4.5] decan-2-one (Example XXIII) (23.6 g) in hexamethylphosphoric triamide (HMPT) is added dropwise to 5 g sodium amide in 35 ml HMPT. The mixture is stirred until NH₃ evolution is essentially finished and 11 ml methyl iodide added at about 40° over a ½ hour period. The mixture is stirred 1 hour, added to 700 ml water and extracted with ethyl acetate. The extract is washed with water, dried and concentrated to give 25 g crude product. A sample of the crude product, recrystallized from cyclohexane, gave the crystalline product, m. 85°–6°.

b. 1-(1-Dimethylaminoethyl)-2-phenylcyclohexanol hydrochloride

A solution of 25.5 g crude 3,4-Dimethyl-6-phenyl-1-oxa-3-azaspiro [4.5] decan-2-one in 125 ml tetrahydrofuran is added to 8 g LiAlH₄ in 300 ml tetrahydrofuran and the mixture refluxed 1¼ hours, cooled and treated with 40 ml water. The mixture is filtered and th filtate washed, dried and concentrated to give 26.6 crude base. A 5 g sample of this crude product is dissolved in 25 ml isopropanol, acidified with HCl gas and diluted with 150 ml ether to give 4.4 g product, m. 206°–7°.

EXAMPLE XXVIII

Preparation of 1-(1-Dimethylaminoethyl)-2-phenylcyclohexyl acetate cyclohexylsulfamate.

1-(1-Dimethylaminoethyl)-2-phenylcyclohexanol (Example XXVII) (20 g) is acylated according to the procedure of Example I (c) using 18 ml acetyl chloride. Conversion of the HCl salt to the cyclohexylsulfamate salt gives 20 g of product, m. 128°–9°.

b.
1-(2-Allylmethylamino-1-methylethyl)-2-phenylcyclohexyl acetate.

The procedure of Example I(c) is followed using 4.8 g of 1-(2-Allylmethylamino-1-methylethyl)-2-phenylcyclohexanol and 13 ml acetyl chloride to give 3.2 g pure product.

EXAMPLE XIV

Preparation of 1-(2-Dimethylaminoethyl)-2-phenylcyclohexanol.

The procedure of Example II is followed except that ethyl-2-bromopropionate is replaced by ethyl bromoacetate and piperidine is replaced by dimethylamine. In this manner, 60 g 2-phenylcyclohexanone and 62 g ethyl bromoacetate gives 20 g of 2-(1-Hydroxy-2-phenylcyclohexyl) acetic acid, m. 122°–5°; 19 g of the acid gives 13.4 g 2-(1-Hydroxy-2-phenylcyclohexyl) ethanol, m. 105°–8°; 13.2 g of the alcohol gives 15.4 g of crude 2-(1-Hydroxy-2-phenylcyclohexyl) ethyl tosylate which gives 10.5 g of 1-(2-Dimethylaminoethyl)-2-phenylcyclohexanol, m. 64°–6°.

EXAMPLE XV

Preparation of 1-(2-Dimethylaminoethyl)-2-phenylcyclohexyl acetate cyclohexylsulfamate.

The procedure of Example I (c) is followed using 7.5 g of 1-(2-Dimethylaminoethyl)-2-phenylcyclohexanol (Example XIV) and 8 ml of acetyl chloride with 18 ml triethylamine giving 11.8 g crude acetate which is treated with 12 g cyclohexanesulfamic acid in tetrahydrofuran to give 6.7 g pure product, m. 140°–1°.

EXAMPLE XVI

Preparation of 1-(2-Diallylamino-1-methylethyl)-2-phenylcyclohexyl acetate.

a.
1-(2-Diallylamino-1-methylethyl)-2-phenylcyclohexanol.

The procedure of Example II is followed except that piperidine is replaced by diallylamine. In this manner, 37 g 2-(1-Hydroxy-2-phenylcyclohexyl) propyl-p-toluenesulfonate and 30 g diallylamine gives 16.2 g product.

b.
1-(2-Diallylamino-1-methylethyl)-2-phenylcyclohexyl acetate.

The procedure of Example I(c) is followed by using 19.7 g of 1-(2-Diallylamino-1-methylethyl)-2-phenylcyclohexanol, 50 ml acetyl chloride, and 75 ml N-methylmorpholine to give 12.8 crude product which gives 3.9 g pure product after chromatography on alumina.

EXAMPLE XVII

Preparation of 1-(2-Dimethylamino-1-methylethyl)-2-(p-methoxyphenyl)-cyclohexanol hydrochloride.

The procedure of Example II is followed except that 2-phenylcyclohexanone is replaced by 2-(p-Methoxyphenyl)cyclohexanone and piperidine is replaced by dimethylene. By this method is obtained 196 g crude Ethyl-2-(1-hydroxy-2-[p-methoxyphenyl]cyclohexyl) propionate from 128.7 g 2-(p-Methoxyphenyl)cyclohexanone (which is prepared by known methods) and 121.8 g Ethyl-2-bromopropionate; 50 g crude 2-(1-Hydroxy-2-[p-methoxyphenyl]cyclohexyl) propionic acid from 196 g Ethyl-2-(1-hydroxy-2-[p-methoxyphenyl]cyclohexyl)propionate; 54.6 g crude 2-(1-Hydroxy-2-[p-methoxyphenyl]cyclohexyl)propanol from 50 g 2-(1-Hydroxy-2-[p-methoxyphenyl]cyclohexyl)propionic acid. The crude 2-(1-Hydroxy-2-[p-methoxyphenyl]cyclohexyl)propanol is converted to the tosylate and treated with 125 ml dimethylamine (according to the procedure of Example II) to give 44 g crude base which is converted to the hydrochloride and recrystallized from isopropanol to give 33.5 g product, m. 245–6.

EXAMPLE XVIII

Preparation of 1-(1-Methyl-2-morpholinoethyl)-2-phenylcyclohexanol hydrochloride.

The procedure of Example II is followed except that piperidine is replaced by morpholine. In this way, 75 g of 2-(1-Hydroxy-2-phenylcyclohexyl) propyl tosylate and 120 ml morpholine gives 59.3 g of the hydrochloride salt, m. 278.

EXAMPLE XIX

Preparation of 1-(1-Methyl-2-morpholinoethyl)2-phenylcyclohexyl acetate hydrochloride.

1-(1-Methyl-2-morpholinoethyl)-2-phenylcyclohexanol hydrochloride (Example XVIII) is converted to the free base and treated with acetyl chloride according to the procedure of Example I (c) using 14 ml acetyl chloride and a reaction time of 90 hours. The product is treated with NaOH to give the base which is dissolved in ether and acidified with HCl gas to give 10.7 g., m. 176.5–7.5 after recrystallization from isopropanol.

EXAMPLE XX

Preparation of
1-(1-Methyl-2-[4-phenyl-1-piperazinyl]ethyl)-2-phenylcyclohexanol.

The procedure of Example II is followed except that piperidine is replaced by 1-phenylpiperazine. In this way 73 g of 2-(1-Hydroxy-2-phenylcyclohexyl)propyl tosylate and 57 g 1-phenylpiperazine give 51 g crude product which is recrystallized from hexane to give the product which melts at 219°–220°.

EXAMPLE XXI

Preparation of
1-(1-Methyl-2-[4-phenyl-1-piperazinyl]ethyl)-2-phenylcyclohexyl acetate hydrochloride.

1-(1-Methyl-2-[4-phenyl-1-piperazinyl]ethyl)-2-phenylcyclohexanol (Example XX) (10 g) is acylated following the procedure of Example I(c) using 20 ml acetyl chloride and a reaction time of approximately 100 hours to give 7.4 g product, m. 180°–1° after recrystallization from 300 ml isopropanol.

EXAMPLE XXIX

Preparation of
1-(2-Dimethylaminoethyl)-2-m-tolyl-cyclohexyl acetate.

The procedure of Example XIV is followed except that 2-phenylcyclohexanone is replaced by 2-m-tolylcyclohexanone. By this method 10.2 g 2-m-tolylcyclohexanone gives 4.4 g crude 1-(1-Hydroxy-2-m-tolycyclohexyl)-acetic acid which is reduced to give 2.0 g 2-(1-Hydroxy-2-m-tolylcyclohexyl)ethanol, m. 50-5; 2.5 g of 2-(1-Hydroxy-2-m-tolylcyclohexyl)ethanol gives 2.5 g crude 2-(1-Hydroxy-2-m-tolylcyclohexyl) ethyl tosylate which gives 2 g crude 1-(2-Dimethylaminoethyl)-2-m-tolylcyclohexanol. Acetylation of this compound following the procedure of Example I(c) gives 2.0 g product.

EXAMPLE XXX

Preparation of
1-(2-Dimethylamino-1-methylethyl)-2-(p-hydroxyphenyl)-cyclohexanol.

1-(2-Dimethylamino-1-methylethyl)-2-(p-methoxyphenyl)cyclohexanol hydrochloride (Example XVII) (7.2 g) is added to a solution of 8.5 g 50% sodium hydride dispersion in 130 ml dimethylformamide with 12.4 g ethanethiol. The mixture is kept at 100° for 9 days, cooled, diluted with 2 volumes of water and 1 volume of saturated NH$_4$Cl solution and extracted 5 times with ether. The ether is washed, dried and concentrated and the residue azeotroped with benzene and concentrated. The residue is washed with ether, dried, and recrystallized from 45 isopropanol to give 3.4 g product, m. 189°–91°.

In an alternate procedure for the preparation of 1-(2-Dimethylamino-1-methylethyl)-2-(p-hydroxyphenyl) cyclohexanol, 51 g ethanethiol in 50 ml dimethylformamide is added dropwise to 35.5 g of 50% sodium hydride in 500 ml dimethylformamide. To this is added 31.8 g of 1-(2-Dimethylamino-1-methylethyl)-2-(p-methoxyphenyl)cyclohexanol hydrochloride. The mixture is then set up for distillation. Distillation is continued until the internal temperature reaches 140°. The mixture is refluxed 5½ hours and then cooled, added to 2 volumes of water and 1 volume of NH$_4$Cl and extracted with 700 ml and 4 × 300 ml ethyl acetate. The extract is washed with water, dried, concentrated, a little ether added and the solid filtered and washed with ether to give 24.7 g product, m. 189°–91°.

EXAMPLE XXXI

Preparation of
1-(2-Dimethylamino-1-methylethyl)-2-(p-hydroxyphenyl)cyclohexyl acetate hydrochloride.

a.
2-(p-Benzyloxyphenyl)-1-(2-dimethylamino-1-methylethyl)cyclohexanol hydrochloride.

1-(2-Dimethylamino-1-methylethyl)-2-(p-hydroxyphenyl)-cyclohexanol (Example XXX) (5.6 g) in 50 ml dimethylformamide is treated with 3.8 g benzyl chloride and 6 g potassium carbonate and stirred 3 hours at 90°. The mixture is cooled, 200 ml water added and extracted with 7×50 ml ethyl acetate. The extract is washed with water, dried and concentrated. The residue is dissolved in 65 ml ethyl acetate and acidified with HCl gas to give 5.7 g product, m. 253°–4°.

b.
2-(p-Benzyloxyphenyl)-1-(2-dimethylamino-1-methylethyl)cyclohexyl acetate.

2-(p-Benzyloxyphenyl)-1-(2-dimethylamino-1-methylethyl)cyclohexanol hydrochloride (11.3 g) is stirred with 140 ml chloroform and 26 g potassium carbonate. Acetyl chloride (6.5 ml) is added and the mixture is stirred overnight, washed with water, and the chloroform dried. The chloroform solution is stirred for 6 hours with 6.5 ml acetyl chloride and 26 g potassium carbonate, then washed with water, dried and concentrated to give 14 g crude product.

c.
1-(2-Dimethylamino-1-methylethyl)-2-(p-hydroxyphenyl)cyclohexyl acetate hydrochloride.

2-(p-Benzyloxyphenyl)-1-(2-dimethylamino-1-methylethyl)cyclohexyl acetate (14 g) in 200 ml acetic acid is reduced catalytically using 5 g Pd/C at 50 psi. The catalyst is filtered off and the filtrate concentrated. The residue is dissolved in chloroform, washed with dilute NaOH, dried and concentrated. The residue is dissolved in 75 ml isopropanol and acidified with HCl gas to give 11.2 g product, m. 218°–19°.

EXAMPLE XXXII

Preparation of
2-(3,4-Dimethoxyphenyl)-1-(2-dimethylamino-1-methylethyl)cyclohexanol p-toluenesulfonate.

The procedure of Example II is followed except that 2-phenylcyclohexanone is replaced by 2-(3,4-Dimethoxyphenyl)cyclohexanone and piperidine is replaced by dimethylamine. In this way, 15 g of 2-(3,4-Dimethoxyphenyl)cyclohexanone gives 14.4 g crude 2-[2-

(3,4-Dimethoxyphenyl)-1-hydroxycyclohexyl] propionic acid which gives 13 g crude 2-[2-(3,4-Dimethoxyphenyl)-1-hydroxycyclohexyl]propanol which gives 21 g crude 2-[2-(3,4-Dimethoxyphenyl)-1-hydroxycyclohexyl]propyl tosylate which is treated with 38 ml dimethylamine to give 12.2 g 2-(3,4-Dimethoxyphenyl)-1-(2-dimethylamino-1-methylethyl)cyclohexanol. The base (4.9 g) is converted to the p-toluenesulfonate by addition of p-toluene sulfonic acid in acetone to an acetone solution of the base to give 3.9 g product, m. 196°–7°.

EXAMPLE XXXIII

Preparation of 2-(3,4-Dimethoxyphenyl)-1-(2-dimethylamino-1-methylethyl)cyclohexyl acetate hydrochloride.

The procedure of Example I(c) is followed using 6.5 ml acetyl chloride and 11.5 g 2-(3,4-Dimethoxyphenyl)-1-(2-dimethylamino-1-methylethyl)cyclohexanol and a reaction time of 6 hours to give 9.5 g. crude HCl salt which is dissolved in 50 ml isopropanol and diluted with 440 ml tetrahydrofuran and 60 ml ether to give 7.1 g product, m. 200°.

EXAMPLE XXXIV

Preparation of [1-(1-Hydroxy-2-phenylcyclohexyl)ethyl]trimethylammonium iodide.

1-(1-Dimethylaminoethyl)-2-phenylcyclohexanol hydrochloride (Example XXVII) (5.6 g) is converted to the base, extracted with chloroform, dried and concentrated to give 4.9 g base. The base is dissolved in 20 ml ethanol, 8 ml methyl iodide added and the mixture heated in a pressure bottle at 65° for 17 hours, then at 95° for 3 hours. The mixture is cooled, 100 ml ethyl acetate added and concentrated to a slurry. Another 100 ml ethyl acetate is added and about half of the solvent is removed on the rotovap. The solid is filtered and washed with ethyl acetate to give 5.9 g product, m. 188-90°.

EXAMPLE XXXV

Preparation of [2-(1-Hydroxy-2-phenylcyclohexyl)propyl]trimethylammonium p-toluenesulfonate.

2-(1-Hydroxy-2-phenylcyclohexyl)propyl p-toluenesulfonate (Example II, Compound III) (10 g) in 75 ml ethanol is stirred at room temperature for 54 hours with 15 ml trimethylamine. The mixture is then heated at 75° for 7 hours in a pressure bottle, concentrated and 125 ml water added. The solution is seeded and the resultant solid filtered and washed to give 6.5 g product, m. 85°–7°.

EXAMPLE XXXVI

Preparation of 1-(2-Dimethylamino-1-methylethyl)-2-phenylcyclohexyl acetate maleate.

a.

1-(2-Dimethylamino-1-methylethyl)-2-phenylcyclohexanol hydrochloride 2-(1-Hydroxy-2-phenylcyclohexyl)propyl-p-toluene sulfonate (Example II, Compound III) (160 g) is dissolved in 1200 ml dimethylsulfoxide. A solution of 160 ml dimethylamine in 240 ml dimethylsulfoxide is added over about 15 minutes and the mixture stirred at room temperature for 3 days, then at 65°–70° for 24 hours. The mixture is poured into 8 liters of water and extracted 3 times with ether. The combined ether extracts are washed with water, dried, and concentrated on the rotovap. The residue is dissolved in 1 liter of dry ether and acidified (cooling below 20°) with a solution of 18 g HCl gas in 100 ml ether. The solid is filtered, washed with ether and dried to give 119 g product, m. 250°–1°.

b.

1-(2-Dimethylamino-1-methylethyl)-2-phenylcyclohexyl acetate maleate 1-(2-Dimethylamino-1-methylethyl)-2-phenylcyclohexanol hydrochloride (119 g) is converted to base which is dissolved in 960 ml chloroform. A solution of 36.2 ml acetyl chloride in 290 ml chloroform is added over a 15 minute period. The mixture is left overnight at room temperature, concentrated to dryness on the rotovap and the residue shaken up with 2 liters of ether. The solid is filtered, washed with ether, dried, dissolved in 1.5 liters of water, made alkaline with 10% NaOH, and extracted with ether. The ether extract is washed with water, dried, and treated with a solution of 76.7 g maleic acid in 192 ml absolute alcohol and 960 ml ether. The mixture is cooled overnight at 10° and filtered to give 108.5 g crude product which is recrystallized twice from isopropanol (4 ml solvent/gm salt), cooling the recrystallization mixture to 10° overnight before filtering off the product in each case. This yields 54.8 gm product melting at 171.5°–172.5°. The identity with the material obtained in Example I(c) is shown by comparison of infrared spectra, elemental analyses and melting point.

PHARMACOLOGY OF 2-ARYL-CYCLOHEXANOL COMPOUNDS

The compounds of this invention were tested for analgesic, local anesthetic and antiarrhythmic activity in experimental animals. Results of analgesic tests are summarized and compared with the standard analgesics morphine and meperidine, etc. in Table I. In addition, general pharmacologic profiles were evaluated and compared with these standards.

Analgesia was assessed in mice utilizing the hot plate method of Eddy and Leimbach, Journal Pharmacology Expt. Therap., 107, 385, 1953, and/or the phenylbenzoquinone writhing method described by Sigmund et al, Proc. Soc. Exptl. Biol. Med., 95, 729, 1957. The hot plate method is based upon the delay in reaction time, following administration of an active analgesic when animals are placed on a heated meal plate maintained at constant temperature. Thus, the numbers of mice showing elevation of response times over control values after administration of various doses of an unknown compound are used to determine the median effective dose ($ED_{50}$), which is that dose affecting 50% of the animals. The writhing method is based upon inhibition by an analgesic of the response which occurs when the chemical agent phenylbenzoquinone is injected intraperitoneally. This response is characterized by a twisting or stretching of the body and is referred to as writhing. Following administration of an analgesic or unknown compound into mice, the numbers of animals not responding to the phenylbenzoquinone challenge by writhing are determined. The $ED_{50}$ can then be calculated to indicate the level of analgesic activity; the lower the $ED_{50}$ value, the more active the compound as an analgesic.

A modification of the method originally described by Irwin (Animal and Clinical Pharmacologic Techniques in Drug Evaluation, Ed. J. H. Nodine and P. E. Siegler, pp 36–54, Philadelphia: Year Book Med. Pub. 1964) was used to establish pharmacologic profiles through use of a multidimensional general screening procedure in mice. This method is based upon direct observation of animals for behavioral changes at intervals after administration of various dose levels of the unknown compound. Qualitative and semiquantitative effects are recorded and comparison is made with profiles of standards. Since active compounds of this invention approach analgesic potency displayed by several narcotic analgesics, morphine and meperidine were used as standards for comparison. Although similar to these standards in several respects, the active compounds of this invention differ in certain qualitative characteristics. In mice, the narcotic analgesics cause stimulation characterized by an increase in locomotor activity. This increased response has been used to estimate the relative levels of morphine-like intrinsic activity of analgesics (Stockhaus, K. E. H. and Villarreal, J. E., 32nd meeting of Committee on Problems of Drug Dependence, Washington, D.C., February 1970, pg 6890 of minutes).

Active compounds of this invention not only failed to cause increased locomotion, but acted in the opposite direction to decrease motility over a wide range of dosage. These results suggest that compounds of this invention might represent a significant advance over existing narcotic analgesics through deviation from certain characteristic morphinelike actions but without sacrificing analgesic effectiveness.

Local anesthetic activity of the compounds of this invention was determined by a study of their effects on the mouse sciatic nerve and by their ability to block conduction of the isolated frog sciatic nerve. Results of these tests are listed in Table I. The most active compound, 1-(2-Dimethylamino-1-methylethyl)-2-phenyl-cyclohexyl acetate maleate (Major isomer) produced sciatic blocks similar to but more prolonged than those produced by lidocaine.

was then given 15 micrograms/kg of ouabain (i.v.) followed by doses of 10 micrograms/kg of ouabain at 15-minute intervals (the last dose of ouabain could be less than 10 micrograms/kg) until an arrhythmia was produced which lasted for 10 minutes. The animal was then given 5 mg/kg (i.v.) of test compound. If the arrhythmia was not reversed after 3 minutes, 1 mg/kg of xylocaine was given (i.v.) to reverse the arrhythmia. If the arrhythmia was reversed within 3 minutes by the test compound, the period of time during which the test compound effected reversal was measured (Arrythmia

TABLE I

| Example No. | Chemical Name | Analgesic Tests | | | | Local Anesthetic Activity |
|---|---|---|---|---|---|---|
| | | $ED_{50}$[1] Hot Plate | | $ED_{50}$ $PBQ_3$ | | |
| | | P.O.[2] | I.P.[2] | P.O. | S.C.[2] | |
| I (a) | 1-(2-Dimethylamino-1-methylethyl)-2-phenylcyclohexyl propionate maleate (Major isomer) | >100 | >40 | 100 | | + |
| I (c) | 1-(2-Dimethylamino-1-methylethyl)-2-phenylcyclohexyl acetate maleate (Major isomer) | 40 | 10 | 20 | 3.8 | + |
| XI | 1-(2-Dimethylamino-1-methylethyl)-2-phenylcyclohexanol p-toluenesulfonate | 56 | 32 | 56 | | + |
| III | 1-(1-Methyl-2-pyrrolidinoethyl)-2-phenylcyclohexanol | | | >100 | ≈30 | + |
| XII | 1-(1-Methyl-2-piperidinoethyl)-2-phenylcyclohexyl acetate hydrochloride | | | ≈60 | ≈30 | + |
| X | (+)-1-(2-Dimethylamino-1-methylethyl)-2-phenycyclohexyl acetate | | | >100 | 16.5 | + |
| IX | (−)-1-(2-Dimethylamino-1-methylethyl)-2-phenylcyclohexyl acetate | | | 16 | 2.15 | |
| XIV | 1-(2-Dimethylaminoethyl)-2-phenylcyclohexanol | | | >100 | ≈30 | |
| XIII | 1-(2-Allylmethylamino-1-methylethyl)-2-phenylcyclohexyl acetate | | | ≈100 | ≈30 | |
| XV | 1-(2-Dimethylaminoethyl)-2-phenylcyclohexyl acetate cyclohexylsulfamate | | | >30 | >10 | + |
| XVI | 1-(2-Diallylamino-1-methylethyl)-2-phenylcyclohexyl acetate | | | >30 | >3 | + |
| XVII | 1-(2-Dimethylamino-1-methylethyl)-2-(p-methoxyphenyl)-cyclohexanol hydrochloride | | | >100 | >30 | + |
| XXXII | 2-(3,4-Dimethoxyphenyl)-1-(2-dimethylamino-1-methylethyl)-cyclohexanol p-toluenesulfonate | | | >100 | ≈30 | |
| XXXIII | 2-(3,4-Dimethoxyphenyl)-1-(2-dimethylamino-1-methylethyl)-cyclohexyl acetate hydrochloride | | | >100 | >30 | + |
| XXII | 1-(1-Methyl-2-pyrrolidinoethyl)-2-phenylcyclohexyl acetate sulfate | | | >30 | ≈10 | + |
| XXI | 1-(1-Methyl-2-[4-phenyl-1-piperazinyl]ethyl)-2-phenyl-cyclohexyl-acetate hydrochloride | | | 5.9 | >100 | |
| XIX | 1-(1-Methyl-2-morpholinoethyl)-2-phenylcyclohexyl acetate hydrochloride | | | 40 | 56.2 | + |
| XXIV | 1-(1-Methylaminoethyl)-2-phenylcyclohexanol hydrochloride | | | >100 | >30 | + |
| XXV | 1-(2-Dimethylamino-1-methylethyl)-2-(p-methoxyphenyl) cyclohexyl acetate hydrochloride | | | >100 | >30 | + |
| XXIII | 1-(1-Aminoethyl)-2-phenylcyclohexanol hydrochloride | | | >100 | >30 | + |
| XXVII | 1-(1-Dimethylaminoethyl)-2-phenylcyclohexanol hydrochloride | | | >100 | >100 | + |
| XXVIII | 1-(1-Dimethylaminoethyl)-2-phenylcyclohexyl acetate cyclohexylsulfamate | | | >30 | >10 | + |
| XXVI | 1-(2-Methylamino-1-methylethyl)-2-phenylcyclohexanol hydrochloride | | | >30 | >10 | + |
| XXX | 1-(2-Dimethylamino-1-methylethyl)-2-(p-hydroxyphenyl)-cyclohexanol | | | >100 | >30 | + |
| XXXI | 1-(2-Dimethylamino-1-methylethyl)-2-(p-hydroxyphenyl)-cyclohexyl acetate hydrochloride | | | >100 | >100 | + |
| Control | Morphine | 18 | 1.8 | 2.6 | 0.5 | − |
| Control | Meperidine | 81 | 5.8 | 18 | 1.7 | + |

[1]$ED_{50}$ — Median Effective Dose mg/kg  
[2]P.O. — Oral Route  
I.P. — Intraperitoneal Route  
S.C. — Subcutaneous Route  
[3]PBQ — Phenylbenzoquinone writhing method Anti-arrhythmic activity was determined by measuring the effect of the test compound in preventing or reversing the arrhythmia produced in dogs or cats by ouabain. In the test method, the animal was pretreated with 10 mg/kg (i.v.) of the test compound. The animal Reversal Time). Results of these tests are given in Table II. With the most active compound, pretreatment of the animal prevented the appearance of arrhythmia when ouabain was given.

TABLE II

| Example No. | Chemical Name | Amount Ouabain μg/kg | Amount Compound mg/kg | Arrhythmia Reversal Time (min.) |
| --- | --- | --- | --- | --- |
| I (c) | 1-(2-Dimethylamino-1-methylethyl)-2-phenylcyclohexyl acetate hydrochloride (Major isomer) | 85 | 4 | 30 |
| XI | 1-(2-Dimethylamino-1-methylethyl)-2-phenylcyclohexanol p-toluenesulfonate | 88 | 4 | 5 |
| III | 1-(1-Methyl-2-pyrrolidinoethyl)-2-phenylcyclohexanol | 100 | 5 | 5 |
| XVII | 1-(2-Dimethylamino-1-methylethyl)-2-(p-methoxyphenyl)-cyclohexanol hydrochloride | 80 | 5 | 30 |
| XXXIII | 2-(3,4-Dimethoxyphenyl)-1-(2-dimethylamino-1-methylethyl)-cyclohexyl acetate hydrochloride | 70 | 5 | 30 |
| XXIV | 1-(1-Methylaminoethyl)-2-phenylcyclohexanol hydrochloride | 140 | 10 mg/kg pretreatment prevented arrhythmia | |
| XXIII | 1-(1-Aminoethyl)-2-phenylcyclohexanol hydrochloride | 95 | 5 | 5 |
| Control | Lidocaine | 60-130 | 1-2 | 1-3 |

We claim:
1. A compound having the formula:

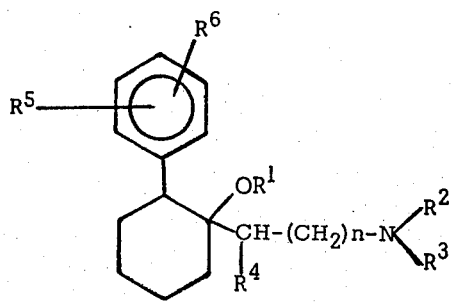

wherein
R¹ is hydrogen or alkanoyl containing 1 to 8 carbon atoms;
R² and R³ individually are hydrogen, alkyl containing 1 to 8 carbon atoms, or lower alkenyl containing 3 to 8 carbon atoms or
R² and R³ together with the nitrogen to which they are attached form a morpholine radical, a piperazine radical or a ring structure containing 3 to 6 methylene groups;
R⁴ is hydrogen or lower alkyl containing 1 to 8 carbon atoms;
R⁵ and R⁶ individually are hydrogen, lower alkyl containing 1 to 8 carbon atoms, hydroxyl, or lower alkoxy containing 1 to 8 carbon atoms;
n is 0 or 1;
the pharmaceutically acceptable acid addition and quaternary salts thereof;
and stereoisomers and optical isomers thereof.
2. The compound of claim 1 wherein R¹ is an alkanoyl radical containing 1 to 8 carbon atoms.
3. The compound of claim 1 wherein R¹ is hydrogen.
4. The compound of claim 1 wherein R² and R³ are alkyl radicals containing 1 to 8 carbon atoms.

5. The compound of claim 1 wherein R² is hydrogen and R³ is an alkyl radical containing 1 to 8 carbon atoms.
6. The compound of claim 1 wherein R² and R³ are hydrogen.
7. The compound of claim 1 wherein R² and R³ together with the nitrogen atom to which they are attached form a piperazine ring.
8. The compound of claim 1 wherein R⁴ is an alkyl radical containing 1 to 8 carbon atoms.
9. The compound of claim 1 wherein R⁵ is an alkoxy radical containing 1 to 8 carbon atoms.
10. The compound of claim 1 wherein R⁵ and R⁶ are alkoxy radicals containing 1 to 8 carbon atoms.
11. The compound of claim 1 wherein n is 0.
12. The compound of claim 1 wherein n is 1.
13. The compound of claim 1 which is 1-(2-dimethylamino-1-methylethyl)-2-phenyl-cyclohexyl acetate hydrochloride.
14. The compound of claim 1 which is 1-(2-dimethylamino-1-methylethyl)-2-phenyl-cyclohexanol p-toluenesulfonate.
15. The compound of claim 1 which is (+)-1-(2-dimethylamino-1-methylethyl)-2-phenyl-cyclohexyl acetate.
16. The compound of claim 1 which is (−)-1-(2-dimethylamino-1-methylethyl)-2-phenyl-cyclohexyl acetate.
17. The compound of claim 1 which is 1-(1-methyl-2-[4-phenyl-1-piperazinyl]-ethyl)-2-phenyl-cyclohexyl acetate hydrochloride.
18. The compound of claim 1 which is 1-(-1-methyl-2-morpholinoethyl)-2-phenyl-cyclohexyl acetate hydrochloride.
19. A compound of claim 1 which is 1-(2-dimethylamino-1-methylethyl)-2-(p-methoxy-phenyl)-cyclohexyl acetate hydrochloride.
20. The compounds of claim 1 which is 1-(2-dimethylamino-1-methylethyl)-2-(p-methoxy-phenyl)-cyclohexanol hydrochloride.
21. The compound of claim 1 which is 2-(3,4-dimethoxy-phenyl)-1-(2-dimethylamino-1-methyl-ethyl)-cyclohexyl acetate hydrochloride.
22. The compound of claim 1 which is 1-(1-methylamino-ethyl)-2-phenyl-cyclohexanol hydrochloride.
23. The compound of claim 1 which is 1-(1-aminoethyl)-2-phenylcyclohexanol hydrochloride.
24. The compound of claim 1 wherein R⁴ is hydrogen.

* * * * *